United States Patent [19]
Thomas et al.

[11] 3,931,311
[45] Jan. 6, 1976

[54] N,N,N-TRISUBSTITUTED N-HALOGENOMETHYLUREA AND THIOUREA COMPOUNDS AND PROCESS FOR THEIR PREPARATION

[75] Inventors: Rudolf Thomas; Wolfgang Kramer, both of Wuppertal; Ludwig Eue, Cologne; Carl Metzger; Gerhard Jager, both of Wuppertal, all of Germany

[73] Assignee: Bayer Aktiengesellschaft, Leverkusen, Germany

[22] Filed: Feb. 21, 1973

[21] Appl. No.: 334,495

[30] Foreign Application Priority Data
Mar. 4, 1972 Germany............................ 2210603

[52] U.S. Cl. ........... 260/552; 260/247.1; 260/247.2; 260/293.85; 260/293.86; 260/453 R; 260/552 R; 260/553 R; 8/88
[51] Int. Cl.² ................. C07C 127/19; C07C 157/02
[58] Field of Search ........ 260/553 A, 453 R, 553 R, 260/552 R

[56] References Cited
UNITED STATES PATENTS
3,505,454    4/1970    Krenzer ................................ 424/272

Primary Examiner—James O. Thomas, Jr.
Assistant Examiner—G. Breitenstein
Attorney, Agent, or Firm—Burgess, Dinklage & Sprung

[57] ABSTRACT
Novel N,N',N'-trisubstituted N-halogenomethylurea compounds of the formula:

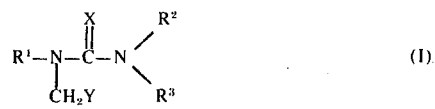

in which
$R^1$ is alkyl, cycloalkyl, cycloalkenyl, bicycloalkyl, bicycloalkenyl, aryl or aralkyl (each of which may be optionally substituted),
$R^2$ is alkyl, alkenyl, alkynyl or alkoxy (each of which may be optionally substituted), or halogenoalkyl or cycloalkyl,
$R^3$ is alkyl (which may be optionally halogen-substituted), alkenyl or alkynyl, or
$R^2$ and $R^3$ jointly represent an alkylene bridge which, can be interrupted by one or more hetero-atoms, such as S or O, or by the NH group, and which forms a heterocyclic ring with the adjoining nitrogen atom,
X is oxygen or sulfur, and
Y is chlorine or bromine.
are prepared by reacting a N,N',N'-trisubstituted urea or thiourea of the general formula:

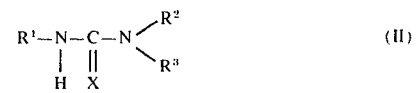

in which
$R^1$, $R^2$, $R^3$ and X have the above-mentioned meanings, is reacted, per mole thereof, with at least 1 mole of formaldehyde (which may be formed in situ from a formaldehyde-releasing substance) and a halogenating agent at a temperature of from $-10°$ to $+150°C$, optionally in the presence of a diluent and, as a catalyst, a proton-releasing compound (for example a hydrogen halide) or a Lewis acid.

7 Claims, No Drawings

N,N,N-TRISUBSTITUTED N-HALOGENOMETHYLUREA AND THIOUREA COMPOUNDS AND PROCESS FOR THEIR PREPARATION

The present invention relates to certain new N,N',N'-trisubstituted N-halogenomethylurea and thiourea compounds. These compounds can be used as intermediate for the production of plant-protection agents and of textile auxiliaries, especially hydrotropic substances. In different aspect, the invention relates to a process for the preparation of such compounds.

It is known that N-halogenoethylureas can be manufactured by reaction of the corresponding N-hydroxyethylureas with thionyl halides (see U.S. Pat. No. 2,985,663); furthermore it is known that bis-N-halogenoethylureas can be obtained in the same manner from bis-N-hydroxymethylureas or from bis-N-hydroxy-ethylureas, respectively (see Melliand, Textilberichte, Heidelberg Vol. 43, Issue 4, 1962, page 382 and J. Medical Chem. Vol. 9, Issue 6, 1966, pages 892–911). These prior-art processes are represented by equations (a) and (b).

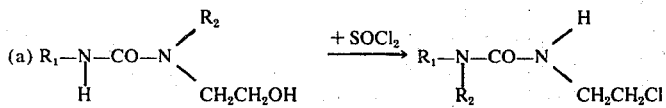

in which
R$_1$ = optionally substituted aryl;
R$_2$ = H or alkyl

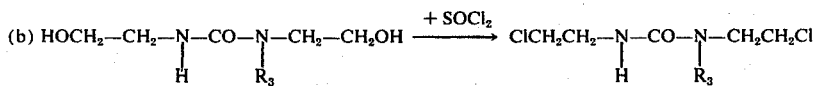

in which
R$_3$ = H or NO.

This reaction has hitherto not been described for the case of N,N',N'-trisubstituted N-hydroxymethylureas.

The present invention provides N,N',N'-trisubstituted N-halogenomethylureas and thioureas of the general formula

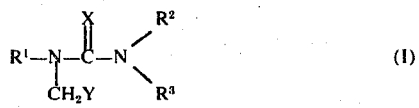

in which
R$^1$ is alkyl, cycloalkyl, cycloalkenyl, bicycloalkyl, bicycloalkenyl, aryl or aralkyl (each of which may be optionally substituted),
R$^2$ is alkyl, alkenyl, alkynyl or alkoxy (each of which may be optionally substituted), or halogenoalkyl or cycloalkyl,
R$^3$ is alkyl (which may be optionally halogen-substituted), alkenyl or alkynyl, or
R$^2$ and R$^3$ jointly represent an alkylene bridge which, can be interrupted by one or more hetero-atoms, such as S or O, or by the NH group, and which forms a heterocyclic ring with the adjoining nitrogen atom,
X is oxygen or sulfur, and
Y is chlorine or bromine.

Generally, R$^1$ contains not more than 14 carbon atoms;
R$^2$ not more than 9, and R$^3$ not more than 6 carbon atoms.

Preferably, R$^1$ is straight-chain or branched alkyl of from 1 to 12 carbon atoms, especially of from 1 to 6 carbon atoms (which alkyl radicals, especially those with 2 to 6 carbon atoms, can be substituted, preferably by halogen, for example fluorine, chlorine or bromine, or by alkyl of from 1 to 3 carbon atoms), cycloalkyl and cycloalkenyl, each of from 5 to 8 ring carbon atoms, and bicycloalkyl and bicycloalkenyl, each with 7 to 10 carbon atoms, (the cycloalkyl, cycloalkenyl, bicycloalkyl and bicycloalkenyl radicals being optionally substituted by alakyl of from 1 to 4 carbon atoms, especially methyl, halogen, especially chlorine, haloalkyl of from 1 or 2 carbon atoms and 1 to 5 halogen atoms, especially chlorine or fluorine, or nitro), optionally substituted aryl of from 6 to 10 carbon atoms, especially phenyl, and aralkyl of from 1 or 2 carbon atoms in the alkylene moiety and 6 to 10 carbon atoms in the aryl moiety, especially benzyl, (preferred substituents for the aryl and aralkyl radicals being halogen, especially fluorine, chlorine and bromine, straight-chain or branched alkyl of from 1 to 4 carbon atoms, halogenalkoxy of from 1 to 4 carbon atoms, alkoxy of from 1 to 4 carbon atoms, alkylthio of from 1 to 4 carbon atoms, especially trifluoromethoxy, halogenoalkyl and halogenoalkylthio each of from 1 or 2 carbon atoms and 2 to 5 halogen atoms, especially trifluoromethyl and chlorodifluoromethylthio, dialkylaminosulfonyl of from 1 or 2 carbon atoms in each alkyl group, alkylthioalkyl of from 1 or 2 carbon atoms in the alkylthio moiety and 1 to 4 carbon atoms in the alkylene moiety, aryloxy of from 6 to 10 carbon atoms (optionally substituted by chlorine and nitro).

R$^2$ is preferably straight-chain or branched alkyl of from 1 to 4 carbon atoms, alkenyl of from 2 to 6 carbon atoms, alkynyl of from 3 to 6 carbon atoms and alkoxy of from 1 to 4 carbon atoms, each of which may be optionally substituted (preferred substituents being alkyl of from 1 to 3 carbon atoms and halogenalkyl of from 1 or 2 carbon atoms and 1 to 3 halogen atoms, especially chlorine or bromine), halogenoalkyl of from 1 to 3 carbon atoms and 1 to 5 halogen atoms, especially chlorine or bromine, and cycloalkyl of from 3 to 6 carbon atoms.

R$^3$ is preferably straight-chain or branched alkyl of from 1 to 4 carbon atoms, which can be substituted by halogen, straight-chain or branched alkenyl of from 2 to 6 carbon atoms and alkynyl of from 3 to 6 carbon atoms, halogenoalkyl of from 1 to 3 carbon atoms and 1 to 5 halogen atoms, especially chlorine and bromine.

R$^2$ and R$^3$ can jointly form a straight-chain or branched methylene bridge of from 3 to 8 members, which can be interrupted by one or more hetero-atoms, such as O or S, or by an NH group, and which forms a heterocyclic ring with the adjoining nitrogen atom.

Furthermore, the present invention provides a process for the production of a compound of the formula (I) in which an N,N',N'-trisubstituted urea or thiourea of the general formula

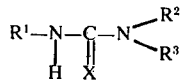

(II), in which $R^1$, $R^2$, $R^3$ and X have the above-mentioned meanings, is reacted, per mole thereof, with at least 1 mole of formaldehyde (which may be formed in situ from a formaldehyde-releasing substance) and a halogenating agent at a temperature of from $-10°$ to $+150°C$, optionally in the presence of a diluent and, as a catalyst, a proton-releasing compound (for example a hydrogen halide) or a Lewis acid.

It is distinctly surprising that monohalogenomethyl derivatives of N,N',N'-trisubstituted ureas are obtained in the process of the invention, since it would have been expected, from the state of the art, that these would be unstable like the corresponding methylol compounds (see Melliand, Textilberichte, Vol 43, Issue 4, page 381, 1962) and would decompose into the starting materials. Instead, the products of the process, which are in general colorless oils and in a few cases low-melting crystalline compounds, are entirely stable on storage in the absence of moisture.

The process according to the invention exhibits a number of advantages. Thus, the production of monohydroxymethyl derivatives, which would have been expected as an intermediate step according to the state of the art, is eliminated. A particularly important fact is that in this way the reactive chloromethyl group can be introduced in an elegant manner without sidereactions occuring at other substitutents of the urea.

If 1-(3,4-dichlorophenyl)-3,3-dimethyl-urea, formaldehyde and thionyl chloride are used as starting materials, the course of the reaction can be represented by the following equation:

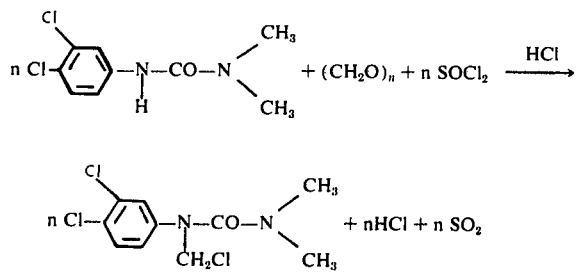

The following may be mentioned as examples of the N,N',N-trisubstituted ureas which can be used according to the invention:

1-propyl-3,3-dimethylurea, 1-butyl-3,3-dimethylurea, 1-[2-methyl-1-propene]-3,3-dimethylurea, 1-cyclooctyl-3,3-dimethylurea, 1-cyclooctyl-3-methyl-3-methoxy-urea, 1-bicycloheptyl-3-methyl-3-methoxyurea, 1-[bicycloheptyl)-methyl]-3,3-dimethylurea, 1-[(3a, 4, 5, 6, 7, 7a-hexahydro)-4,7-methanoindan-5-yl]-3,3-dimethylurea, 1-[(3a,4, 5, 6, 7, 7a-hexahydro)-4,7-methano-indan-2-yl]-3,3-dimethylurea, 1-[(3a, 4, 5, 6, 7, 7a-hexahydro)-4,7-methano-indan-1-yl]-3,3-dimethylurea, 1-(5-nitro-3-methyl-norbornyl-2)-3,3-dimethylurea, 1-bicyclo-(3,3,0)octyl-3,3-dimethylurea, 1-(3,4-dichlorophenyl)-3-dimethyl-3-(1'-methyl-prop-2-ynyl)-urea, 1-(3,4-dichlorophenyl)-3-piperidinourea, 1-(3-chloro-benzyl)-3,3-dimethylurea, 1-(3,4-dichloro-benzyl)-3,3-dimethylurea, 1-phenyl-3,3-dimethylurea, 1-(4-chlorophenyl)-3-methyl-3-methoxy-urea, 1-(3,4-dichlorophenyl)-3,3-dimethylurea, 1-(3,4-dichlorophenyl)-3-methyl-3-methoxyurea, 1-(3,4-dichlorophenyl)-3-butyl-3-methyl-urea, 1-(3,4-dichlorophenyl)-3-methyl-3-propyn-(2)-ylurea, 1-(3,4-dichlorophenyl)-3-morpholino-urea, 1-(4-methylphenyl)-3,3-dimethylurea, 1-(3-trifluoromethylphenyl)-3,3-dimethylurea, 1-(4-trifluoromethylphenyl)-3,3-dimethylurea, 1-(3-chloro-4-trifluoromethylphenyl)-3,3-dimethylurea, 1-(4-chloro-3-trifluoromethylphenyl)-3,3-dimethylurea, 1-(3-chloro-4-difluorochloromethylmercaptophenyl)-3,3-dimethylurea, 1-(3-chloro-4-methylphenyl)-3,3-dimethylurea, 1-(4-chloro-3-nitrophenyl)-3,3-dimethylurea, 1-(4-chloro-3-methylthiophenyl)-3,3-dimethylurea, 1-(4-ethoxyphenyl)-3,3-dimethylurea, 1-(4-butoxyphenyl)-3,3-dimethylurea, 1-(3-chloro-4-methoxyphenyl)-3,3-dimethylurea, 1-(4,4'-chlorophenoxyphenyl)-3,3-dimethylurea, 1-(3-chloro-4-methylthiomethyl-phenyl)-3,3-dimethylurea, 1-(4-dimethylaminosulphonylphenyl)-3,3-dimethylurea, 1-(phenyl)-3,3-dimethylurea, 1-(4-bromophenyl)-3-methoxy-3-methyl-urea, 1-(3-methylphenyl)-3,3-dimethylthiourea, 1-(4-chlorophenyl)-3,3-dimethylthiourea, 1-(3,4-dichlorophenyl)-3,3-dimethylthiourea and 1-(3-chloro-4-bromophenyl)-3-methoxy-3-methylurea.

The ureas and thioureas used as starting substances are in most cases known; those which have not yet been described in the literature can be prepared according to known processes (see Angewandte Chemie 75 (1963), pages 851–854).

The other starting materials, namely formaldehyde or formaldehyde-releasing substances, such as formalin, trioxane and paraformaldehyde, are also known.

As diluents for the reaction according to the invention, all inert organic solvents are suitable, especially hydrocarbons such as petroleum ether, ligroin and toluene, halogenated hydrocarbons such as chlorobenzene, 1,2-dichlorobenzene, 1,2-dichloroethane, methylene chloride and chloroform, nitrated hydrocarbons such as nitrobenzene and nitromethane, and ethers such as diethyl ether.

Possible halogenating agents are organic or inorganic acid halides, but preferably oxalyl chloride, acetyl chloride, acetyl bromide, phthaloyl chloride, thionyl chloride, thionyl bromide, phosphorus trichloride, phosphorus tribromide, phosphorus oxychloride, phosphorus pentachloride or phosphorus pentabromide is used. It is, however, also possible to use organic compounds which possess activated halogen atoms, for example, α,α dichloromethyl-methyl-ether, as the halogenating agents. The use of the above-mentioned inorganic acid halides phosphorus trichloride, phosphorus tribromide and thionyl chloride is particularly advantageous.

Proton-releasing compounds or Lewis acids are preferably employed as catalysts. As examples there may be mentioned: hydrogen chloride, hydrogen bromide, iron(III) chloride and zinc(II) chloride. In some cases it is advantageous to use a combination of the catalysts mentioned.

The reaction temperatures can be varied over a fairly wide range. In general, the reaction is carried out at from −10° to +150°C, preferably from +10° to +60°C.

The pressure can also be varied over a fairly wide range. In general, normal pressure is used but it is also possible to employ excess pressures of about 1.1 atmospheres to about 5 atmospheres.

In carrying out the process according to the invention, 1 to 1.5 moles of formaldehyde (as such or produced from a formaldehyde-releasing substance), 1 to 1.5 moles of halogenating agent and 0.1 to 5 moles of catalyst (if used) are usually employed per 1 mole of starting material of the formula (II). Exceeding the stoichiometric ratios by more than this does not result in any significant improvement in yield.

To isolate the compounds of the formula (I), the solvent is distilled off in vacuo with exclusion of moisture. Any excess of formaldehyde is already removed during the reaction by a corresponding excess of halogenating agent, since the reaction of these two components results in gaseous products, such as hydrogen chloride and sulfur dioxide, which escape, and also methylene chloride, which can be distilled off. The residue is treated with carbon tetrachloride if appropriate and the solvent is distilled off. In general an oily residue is obtained, in a few cases a low melting crystalline precipitate results. This is purified by recrystallization if desired.

The process according to the invention permits the preparation of previously unknown N-halogenomethylureas and thioureas which are capable of numerous further reactions and which can therefore inter alia be employed as intermediate products for the manufacture of plant-protection agents. The new N-halogenomethylureas and thioureas can furthermore, after reaction with ethylene glycol, be employed as auxiliaries for dyeing processes (hydrotropic substances) (see Example 34) and are therefore of great importance for the preparation of textile auxiliaries.

The process according to the invention is illustrated by the following examples:

EXAMPLES 1

Preparation of
1-chloromethyl-1-phenyl-3,3-dimethylurea

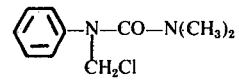
(1)

164 g (1 mole) of 1-phenyl-3,3-dimethylurea and 45 g (1.5 moles) of paraformaldehyde were suspended in 1,500 ml of anhydrous benzene. This suspension was saturated with dry hydrogen chloride gas by passing in the latter at a temperature of 10° to 15°C. Thereafter 179 g (1.5 moles) of thionyl chloride were slowly added dropwise at a temperature of 15° to 20°C whilst stirring and cooling with ice.

After stirring overnight at room temperature, the solvent is distilled off in vacuo at 40°C bath temperature, whilst excluding moisture. The residue was treated with 100 ml of carbon tetrachloride, the mixture was filtered and the filtrate was distilled off in vacuo. The resulting oil was dried in a high vacuum.

212.5 g of 1-chloromethyl-1-phenyl-3,3-dimethylurea were obtained in quantitative yield. The compound was best characterized by its proton resonance spectrum (PMR): the chemical displacement δ of the $CH_2$ group

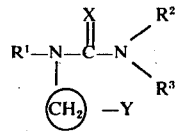

newly formed in the reaction according to the invention, measured at 60 MHz in carbon tetrachloride as the solvent and against tetramethylsilane (TMS) (δ= 0 ppm) as the internal standard was 5.58 ppm.

The compounds listed in Table 1, below were prepared in a manner analogous to that described in Example 1; they are again best characterized by the chemical displacement ("δ -value" in ppm) of the newly formed $CH_2$ protons as a physio-chemical characteristic value.

Table 1

$$R^1-N-\overset{\overset{X}{\|}}{C}-N\overset{R^2}{\underset{R^3}{\diagdown}}$$
$$\underset{CH_2-Y}{|}$$
(I)

| Example No. | R¹ | R² | R³ | X | Y | δ-value (ppm), 60 MHz, TMS as internal standard* (solvent) |
|---|---|---|---|---|---|---|
| 2 | 2,4-Cl₂-C₆H₃- | OCH₃ | CH₃ | O | Cl | 5.46 (CCl₄) |
| 3 | 4-Cl-C₆H₄- | CH₃ | CH₃ | O | Cl | 5.49 (CCl₄) |
| 4 | 4-Cl-C₆H₄- | OCH₃ | CH₃ | O | Cl | 5.44 (CCl₄) |

Table 1-continued $$R^1-N-\overset{\overset{X}{\|}}{C}-N\overset{R^2}{\underset{R^3}{\diagdown}}$$
$$\underset{CH_2-Y}{|}$$
(I)

| Example No. | R¹ | R² | R³ | X | Y | δ-value (ppm), 60 MHz, TMS as internal standard*) (solvent) |
|---|---|---|---|---|---|---|
| 5 | 3,4-dichlorophenyl 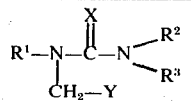 | CH₃ | CH₃ | O | Cl | 5.61 (CDCl₃); Melting point 35°C |
| 6 | 3-CF₃-phenyl 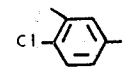 | CH₃ | CH₃ | O | Cl | 5.67 (CDCl₃) |
| 7 | 3-Cl-4-CH₃O-phenyl 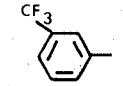 | CH₃ | CH₃ | O | Cl | 5.56 (CDCl₃) |
| 8 | 3-Cl-4-CH₃-phenyl 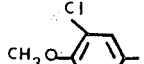 | CH₃ | CH₃ | O | Cl | 5.58 (CDCl₃) |
| 9 | 4-(4-chlorophenoxy)phenyl 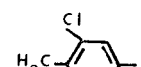 | CH₃ | CH₃ | O | Cl | 5.62 (CDCl₃) |
| 10 | 3-Cl-4-CF₃-phenyl 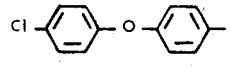 | CH₃ | CH₃ | O | Cl | 5.69 (CDCl₃) |
| 11 | 3-Cl-4-CF₃O-phenyl 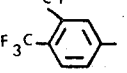 | CH₃ | CH₃ | O | Cl | 5.63 (CDCl₃) |
| 12 | 3-Cl-4-NO₂-phenyl 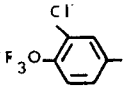 | CH₃ | CH₃ | O | Cl | 5.61 (CDCl₃) |
| 13 | 3-Cl-4-SCH₃-phenyl 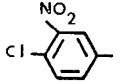 | CH₃ | CH₃ | O | Cl | 5.54 (CDCl₃) |
| 14 | 4-C₂H₅O-phenyl 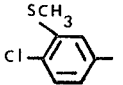 | CH₃ | CH₃ | O | Cl | 5.60 (CDCl₃) |
| 15 | 4-(CH₃)₂N-O₂S-phenyl-CH₃ 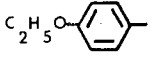 | CH₃ | CH₃ | O | Cl | 5.63 (CDCl₃) |

Table 1-continued $$R^1-N-\underset{\underset{CH_2-Y}{|}}{\overset{\overset{X}{\|}}{C}}-N\underset{R^3}{\overset{R^2}{<}} \quad (I)$$

| Example No. | R¹ | R² | R³ | X | Y | δ-value (ppm), 60 MHz, TMS as internal standard*) (solvent) |
|---|---|---|---|---|---|---|
| 16 | H₃C–C₆H₄– | CH₃ | CH₃ | O | Cl | 5.57 (CDCl₃) |
| 17 | 3,4-Cl₂C₆H₃– | C₄H₉ | CH₃ | O | Cl | 5.59 (CDCl₃) |
| 18 | 3,4-Cl₂C₆H₃– | morpholino | | O | Cl | 5.58 (CDCl₃) |
| 19 | 3,4-Cl₂C₆H₃– | CH₃ | CH₃ | S | Cl | 5.58 (CDCl₃) |
| 20 | 4-ClC₆H₄– | C₄H₉ | C₄H₉ | O | Cl | 5.59 (CDCl₃) |
| 21 | 4-ClC₆H₄– | –CH₂–CH=CH₂ | –CH₂–CH=CH₂ | O | Cl | 5.63 (CDCl₃) |
| 22 | 4-ClC₆H₄– | CH₃ | CH₃ | S | Cl | 5.59 (CDCl₃) |
| 23 | 4-ClC₆H₄– | –CH(CH₃)–C≡CH | CH₃ | O | Cl | 5.60 (CDCl₃) |
| 24 | F₃C–C₆H₄– | CH₃ | CH₃ | O | Cl | 5.74 (CDCl₃) |
| 25 | 2-CF₃-4-Br-C₆H₃– | CH₃ | CH₃ | O | Cl | 5.68 (CDCl₃) |
| 26 | C₆H₅– | CH₂CH₂Cl | CH₂CH₂Cl | O | Cl | 5.61 (CDCl₃) |
| 27 | 2,3-Cl₂C₆H₃– | CH₂–CH=CH₂ | CH₂–CH=CH₂ | O | Cl | 5.62 (CDCl₃) |
| 28 | C₆H₅–CH₂– | CH₃ | CH₃ | O | Cl | 5.49 (CDCl₃) |

Table 1-continued $$R^1-N(CH_2-Y)-C(=X)-N(R^2)(R^3) \quad (I)$$

| Example No. | R¹ | R² | R³ | X | Y | δ-value (ppm), 60 MHz, TMS as internal standard*) (solvent) |
|---|---|---|---|---|---|---|
| 29 | (norbornyl-CH₂–) | CH₃ | CH₃ | O | Cl | 5.41 (CDCl₃) |
| 30 | (2,6-dimethylcyclohexyl) | CH₃ | CH₃ | O | Cl | 5.40 (CDCl₃) |
| 31 | (cyclooctyl) | CH₃ | CH₃ | O | Cl | 5.39 (CDCl₃) |
| 32 | C₄H₉ | CH₃ | CH₃ | O | Cl | 5.35 (CDCl₃) |
| 33 | (2,6-diethylphenyl) | CH₃ | CH₃ | O | Cl | 5.59 ppm |

*)compare Example 1

EXAMPLE 34

Preparation of 1-β-hydroxy-ethoxymethyl-1-phenyl-3,3-dimethylurea

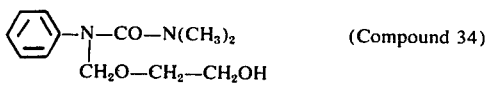 (Compound 34)

212 g (1 mole) of 1-chloromethyl-1-phenyl-3,3-dimethylurea were dissolved in 100 ml of anhydrous ethyl acetate and 63 g (1.0 mole) of ethylen glycol and 60 g (1.0 mole) of triethylamine were added dropwise whilst cooling with ice. After stirring for 2 hours at 10° to 15°C, the triethylamine hydrochloride used was filtered off and the solvent was distilled off. 238 g of 1-β-hydroxyethoxymethyl-1-phenyl-3,3-dimethylurea were obtained as an oil, in quantitative yield.

1-β-Hydroxy-ethoxymethyl-1-phenyl-3,3-dimethylurea can be used, for example, in the following padding liquor mixture:

20 – 40 g of pigment dyestuff paste, 10–20% strength
50 g of tragacanth, 6% strength
30 g of 1-β-hydroxyethoxymethyl-1-phenyl-3,3-dimethylurea
10 g of ammonia, 25% strength
8 g of ammonium thiocyanate
100 g of Buna emulsion
782–762 g of water
1,000 g Total It will be understood that the specification and examples are illustrative but not limitative of the present invention and that other embodiments within the spirit and scope of the invention will suggest themselves to those skilled in the art.

What is claimed is:

1. N,N′,N′-trisubstituted N-halogenomethylurea compound of the formula

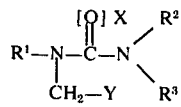

in which
X is oxygen or sulfur
R¹ is phenyl, unsubstituted or substituted with chlorine, bromine, trifluoromethyl, trifluoromethoxy, nitro, methyl, ethyl, methoxy, methylthio, ethoxy or chlorophenoxy,
R² and R³ are selected from the group of methyl, butyl, allyl,

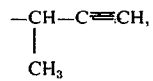

and chloroethyl,
and Y is chlorine.

2. Compound as claimed in claim 1 wherein R¹ is 4-chlorophenyl or 3,4-dichlorophenyl, R² and R³ are methyl, X is sulfur and Y is chlorine.

3. Compound as claimed in claim 1 wherein R¹ is 4-chlorophenyl or 3,4-dichlorophenyl, R² is methoxy, R³ is methyl, X is oxygen, and Y is chlorine.

4. Compound as claimed in claim 1 designated 1-chloromethyl-1-phenyl-3,3-dimethylurea.

5. Compound as claimed in claim 1 designated 1-chloromethyl-1-(3,4-dichlorophenyl)-3-methoxy-3-methylurea.

6. Compound as claimed in claim 1 designated 1-chloromethyl-(4-chlorophenyl)-3,3-dimethylurea.

7. Compound as claimed in claim 1 designated 1-chloromethyl-1-(3,4-dichlorophenyl)-3,3-dimethylurea.

* * * * *